US000001142H

United States Statutory Invention Registration [19]

[11] Reg. Number: H1142

[43] Published: Feb. 2, 1993

Slusarchyk et al.

[54] OPTICALLY ACTIVE CYCLOBUTYL PYRIMIDINE

[76] Inventors: William A. Slusarchyk, 19 Richmond Dr., Skillman, N.J. 08558; Robert Zahler, 16 Park Pl., Princeton, N.J. 08542

[21] Appl. No.: 608,780

[22] Filed: Nov. 5, 1990

[51] Int. Cl.[5] ..... C07D 239/02

[52] U.S. Cl. ..... 544/314

[58] Field of Search ..... 544/314

[56] References Cited

U.S. PATENT DOCUMENTS 4,564,618 1/1986 Scopes et al. ..... 544/314
5,064,961 1/1991 Bisacchi et al. ..... 544/276

FOREIGN PATENT DOCUMENTS 0335355 3/1989 European Pat. Off. .
0358154 3/1990 European Pat. Off. .
0366059 10/1990 European Pat. Off. .

OTHER PUBLICATIONS

Bodenteich et al. Chem. Abst. 108-187146r (1958).
Haralambidis et al. Chem. Abst. 111-39836n (1989).
Griengl et al. Journal of Medicinal Chemistry vol. 28, No. 11, p. 1679 (1985).

*Primary Examiner*—Robert L. Stoll
*Assistant Examiner*—Joseph D. Anthony

[57] ABSTRACT

The compound of the formula

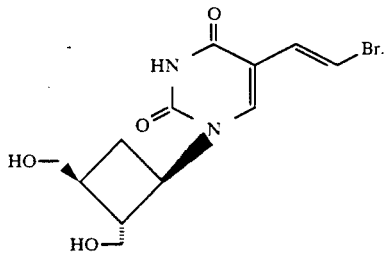

1

[1R-(1α(E),2β,3α)]-1-[2,3-bis(hydroxymethyl)cyclobutyl]-5-(2-bromoethenyl)-2,4(1H,3H)-pyrimidinedione, is an antiviral agent that is active against herpes simplex virus 1 and varicella-zoster virus.

1 Claim, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

OPTICALLY ACTIVE CYCLOBUTYL PYRIMIDINE

DETAILED DESCRIPTION OF THE INVENTION

1

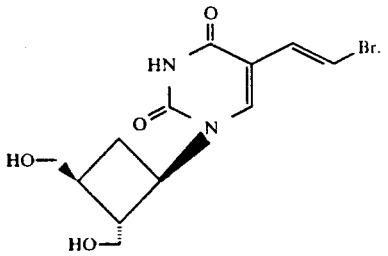

[1R-(1α(E),2α,3α)]-1-[2,3-bis(hydroxymethyl)cyclobutyl]-5-(2-bromoethenyl)-2,4(1H,3H)-pyrimidinedione, is an antiviral agent that is active against herpes simplex virus 1 and varicella-zoster virus. It can be used to treat viral infections in humans and other mammals.

The compounds of this invention may be administered parenterally (for example, by intravenous, intraperitoneal or intramuscular injection), orally or topically depending on whether the preparation is used to treat internal or external viral infections.

For internal infections, the compounds may be administered orally or parenterally in an amount effective to treat the infection. The dosage will, of course, depend on the severity of the infection, but will likely be in the range of about 1.0 to 50 mg/kg of body weight. The desired dose may be administered several times daily at appropriate intervals.

For infections of the eye, or other external tissues, e.g. mouth and skin, the compositions may be applied to the infected part of the body of the patient topically as an ointment, cream, aerosol, gel, powder, lotion, suspension or solution (e.g. as in eye drops). The concentration of the compound in the vehicle will, or course, depend on the severity of the infection, but will likely be in the range of about 0.1 to 7% by weight.

The compound of formula 1 can be prepared as follows: Reaction of diethylfumarate and ketene diethylacetal in hot t-butanol, yields the compound of formula

2

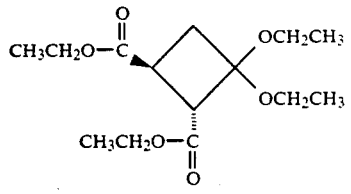

as a racemic mixture (see K. C. Brannock et al., J. Org. Chem., 29, 940 (1964)). Treatment of the compound of formula 2 with alkali (e.g. potassium hydroxide) in a mixed aqueous organic solvent such as water-tetrahydrofuran-methanol provides, after acidification, the racemic mixture of formula

3

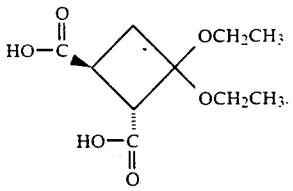

Treatment of the racemic mixture of formula 3 with a chiral primary amine such as R-(−)-2-phenylglycinol in the presence of a coupling agent (e.g. 1,3-dicyclohexylcarbodiimide) in a solvent such as dichloromethane provides a mixture of two homochiral compounds of formulas

4

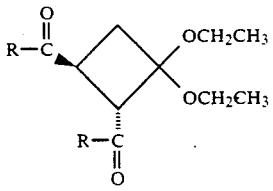

and

5

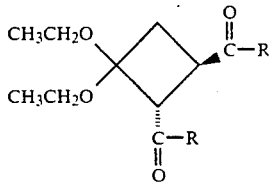

wherein R is

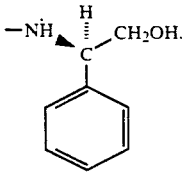

The compounds of formulas 4 and 5 are diasteriomeric and can be separated by chromatography (e.g. on silica gel) or by crystallization from various solvents and solvent mixtures such a dichloromethane, dichloromethane-ether, and the like. Protection of the hydroxyl groups in the chiral compound of formula 4 with a hindered silyl group such as t-butyldimethyl silyl (e.g., by treatment with t-butyldimethylsilyl chloride and imidazole in dimethylformamide) affords the homochiral compound of formula 4 wherein R is

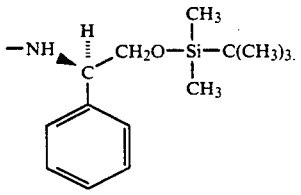

Reaction of this compound of formula 4 with a suitable nitrosating agent such as nitrogen tetroxide ($N_2O_4$) in a solvent such as carbon tetrachloride in the presence of sodium acetate provides the homochiral compound of formula 4 wherein R is

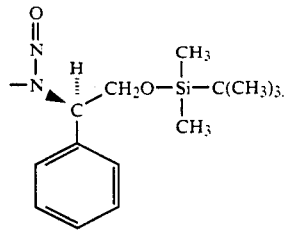

Treatment of this compound of formula 4 with a reducing agent such as lithium borohydride in a solvent such as tetrahydrofuran or diethyl ether yields the homochiral compound of formula

6

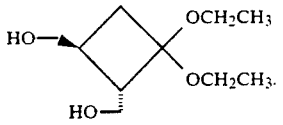

Protection of the hydroxyl groups in the compound of formula 6 with a benzoyl group using, for example, benzoyl chloride in a solvent such as pyridine, provides the homochiral compound of formula

7

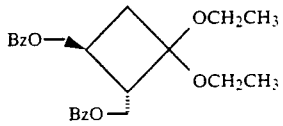

wherein Bz is a benzoyl group.

Treatment of the compound of formula 7 with an acid catalyst such as sulfuric acid or p-toluenesulfonic acid in a solvent or solvent mixture such as water, water-acetonitrile, water-dioxane, or acetone yields the homochiral compound of formula

8

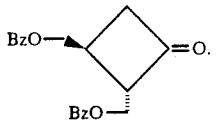

Reaction of the compound of formula 8 with a hindered reducing agent such as lithium trisiamylborohydride or lithium tri-sec-butylborohydride in a solvent such as tetrahydrofuran or ether provides the homochiral compound of formula

9

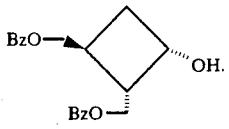

Treatment of the compound of formula 9 with p-toluenesulfonyl chloride in a solvent such as pyridine affords the homochiral compound of formula

10

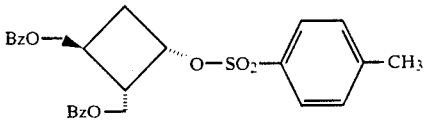

Treatment of the compound of formula 10 with the tetrabutylammonium salt of uracil in an aprotic polar solvent such as dimethylformamide yields the homochiral compound of

11

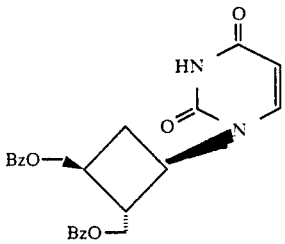

Removal of the benzoyl protecting groups from the compound of formula 11 by treatment with sodium methoxide in methanol provides the homochiral compound of formula

12

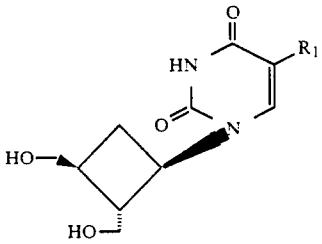

wherein $R_1$ is hydrogen.

Iodination of the compound of formula 12 wherein $R_1$ is hydrogen with iodine and aqueous nitric acid in dioxane gives the homochiral compound of formula 12 wherein $R_1$ is iodo. Treatment of the compound of formula 12 wherein $R_1$ is iodo with methyl acrylate in dioxane in the presence of palladium (II) acetate, triphenylphosphine, and triethylamine affords the homochiral compound of formula 12 wherein $R_1$ is

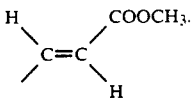

Saponification of the methyl ester group in the compound of formula 12 wherein $R_1$ is

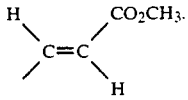

by treatment with aqueous potassium hydroxide and subsequent acidification provides the homochiral compound of formula 12 wherein $R_1$ is

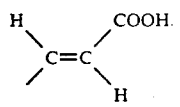

Treatment of the compound of formula 12 wherein $R_1$ is

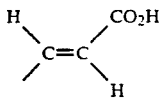

with N-bromosuccinimide in a polar aprotic solvent such as dimethylformamide in the presence of a base such as potassium bicarbonate affords the desired homochiral compound of formula 1, [1R-(1α(E),2β,-3α)]-1-[2,3-bis(hydroxymethyl)cyclobutyl]-5-(2-bromoethenyl)-2,4(1H,3H)-pyrimidinedione.

EXAMPLE 1

[1R-(1α(E),2β,3α)]-1-[2,3-bis(hydroxymethyl)cyclobutyl]-5-(2-bromoethenyl)-2,4(1H,3H)-pyrimidinedione

Example 1a trans-3,3-Diethoxy-1,2-cyclobutanedicarboxylic acid, diethyl ester (racemic mixture)

A mixture of diethylketene acetal (38.35 g) and diethylfumarate (53.5 ml) in t-butanol (90 ml) was heated at 84° C. for 72 hours. Distillation of the reaction mixture (113°–125° C., 0.6–1.6 mm Hg) afforded 50.4 g of product.

Example 1b trans-3,3-Diethoxy-1,2-cyclobutanedicarboxylic acid (racemic mixture)

A solution of trans-3,3-diethoxy-1,2-cyclobutanedicarboxylic acid, diethyl ester (100 g) in 1400 ml of tetrahydrofuran under argon was treated with 1400 ml of methanol and 1400 ml of 1N potassium hydroxide solution. The resulting mixture was allowed to stand for 3 days at room temperature and then was evaporated in vacuo to an aqueous solution. The pH was adjusted to 2.3 with 3N hydrochloric acid, and the solution was saturated with sodium chloride. The resulting suspension was extracted with ethyl acetate (3×1000 ml). The combined extracts were washed with 250 ml of water and 250 ml of brine, dried over sodium sulfate, and evaporated to afford the product as solid, 78.8 g, m.p. 118°–120° C.

Example 1c

[1S-[1α(S*),2β(S*)]]-3,3-Diethoxy-N,N'-bis(2-hydroxy-1-phenylethyl)-1,2-cyclobutanedicarboxamide A suspension of 60.0 g of trans-3,3-diethoxy-1,2-cyclobutanedicarboxylic acid in 500 ml of methylene chloride under argon was treated with 92.4 g of R-(−)-2-phenylglycinol. The resulting solution was cooled in an ice bath and treated with 120 g of 1,3-dicyclohexylcarbodiimide. The mixture was stirred overnight at ambient temperature and then was diluted with 1500 ml of diethyl ether and filtered. The filtrate was washed with 10% sodium bisulfate (twice), saturated sodium bicarbonate (twice) and brine (twice). The organic phase was dried over sodium sulfate and evaporated to a semi-solid which was chromatographed on a column of silica gel (2.5 L), eluting with ethyl acetate-hexane followed by methanol-ethyl acetate. Combination of appropriate fractions gave a mixture of the two isomers, [1S-[1α(S*),2β(S*)]]-3,3-Diethoxy-N,N'-bis(2-hydroxy-1-phenylethyl)-1,2-cyclobutanedicarboxamide and [1S-[1α(R*),2β(R*)]]-3,3-diethoxy-N,N'-bis(2-hydroxy-1-phenylethyl)-1,2-cyclobutanedicarboxamide as a foam (88.7 g). This mixture was dissolved almost completely in 600 ml of methylene chloride with heating. This solution was chilled at 5° C. for 4 hours and the resulting solid was filtered and washed with 150 ml of cold methylene chloride. Drying in vacuo gave 31 g of solid. Concentration of the mother liquors and chilling at −30° C. for 12 hours gave a second crop of solid title compound. Similar mixtures of [1S-[1α(S*),2β(S*)]] and [1R-[1α(R*),2β(R*)]]-3,3-diethoxy-N,N'-bis(2-hydroxy-1-phenylethyl)-1,2-cyclobutanecarboxamide from several preparations were combined (98.1 g) and heated with 2500 ml of methylene chloride until nearly completely dissolved. The solution was chilled at 5° C. overnight and filtered, and the solid was washed with 500 ml of cold methylene chloride. Drying in vacuo gave 83 g of the desired product, which was completely free of [1R-[1α(R*), 2β(R*)]]-3,3-diethoxy-N,N'-bis-(2-hydroxy-1-phenylethyl)-1,2-cyclobutanedicarboxamide, as judged by HPLC. The mother liquor was concentrated to 150 ml, heated to partially dissolve solids, and then cooled in an ice bath for 1 hour. The resulting solid was filtered and washed with 50 ml of cold methylene chloride and dried in vacuo to give an additional 11.8 g of isomerically pure title compound. An analytical sample was obtained by recrystallization from ethyl acetate, m.p. 128°–129° C., $[\alpha]_D$ −16.8° (c=1.00, methanol). The absolute stereochemistry of the product was ascertained by X-ray crystallographic analysis (crystals obtained by recrystallization from water).

Example 1d

[1S-[1α(S*),2β(S*)]]-N,N'-Bis[2-[[(1,1-dimethylethyl)-dimethylsilyl]oxy]-1-phenylethyl]-3,3-diethoxy-1,2-cyclobutanedicarboxamide A slurry of 23.5 g of [1S-[1α(S*),2β(S*)]]-3,3-diethoxy-N,N'-bis(2-hydroxy-1-phenylethyl)-1,2-cyclobutanedicarboxamide and 13.6 g of imidazole in 100 ml dry dimethylformamide under nitrogen was cooled to 0° C. and treated with 15.8 g of solid t-butyldimethylsilyl chloride. After stirring at 0° C. for 1.5 hours, the mixture was diluted to 600 ml with ethyl acetate and washed with 3% hydrochloric acid (thrice), water (once), and brine (twice). Drying over sodium sulfate and evaporation gave an oily solid. This was taken up in 50 ml of ethyl acetate and diluted with 200 ml of hexane. The resulting slurry was filtered and the cake was washed with 100 ml of 20% ethyl acetate in hexane. Evaporation of the filtrate in vacuo afforded the title compound as a clear glass, 33.6 g.

Example 1e

[1S-[1α(S*),2β(S*)]]-N,N'-Bis[2-[[(1,1-dimethylethyl)-dimethylsilyl]oxy]-1-phenylethyl]-3,3-diethoxy-N,N'-dinitroso-1,2-cyclobutanedicarboxamide A solution of 33.6 g of 1S-[1α(S*),2β(S*)]]-N,N'-bis[2-[[(1,1-dimethylethyl)dimethylsilyl]-oxy]-1-phenylethyl]-3,3-diethoxy-1,2-cyclobutanedicarboxamide in 250 ml of dry carbon tetrachloride was treated with 35 g of fresh anhydrous sodium acetate. The resulting slurry was chilled in an ice bath and treated with stirring over 15 minutes with 75 ml of a 2.76M solution of nitrogen tetroxide in carbon tetrachloride. The resulting yellow mixture was stirred for another 15 minutes at 0° C. and then was poured into a mixture of ice (500 ml), water (200 ml), sodium acetate trihydrate (100 g), and methylene chloride (500 ml). The mixture was shaken for a few minutes and the resulting yellow organic layer was separated and washed with brine. Drying over magnesium sulfate and evaporation in vacuo at <15° C. gave 46.6 g of the title compound as a thick yellow oil.

Example 1f (1S-trans)-3,3-diethoxy-1,2-cyclobutanedimethanol 46.6 g of [1S-[1α(S*),2β(S*)]]-N,N'-Bis[2-[[(1,1-dimethylethyl)dimethylsilyl]-oxy-1-phenylethyl]-3,3-diethoxy-N,N'-dinitroso-1,2-cyclobutanedicarboxamide, was dissolved in 200 ml of dry tetrahydrofuran and the resulting solution was chilled at 0° C. and cannulated into a 0° C. solution of lithium borohydride in tetrahydrofuran (150 ml of a 2M solution). The addition took 15 minutes after which the cooling bath was removed, and the clear orange mixture was allowed to stir at ambient temperature overnight. The resulting nearly colorless solution was chilled in an ice bath while being treated with 25 ml of water dropwise. The resulting slurry was diluted with 500 ml of diethyl ether and water was added to dissolve most of the solid (100 ml). The layers were separated and the aqueous layer was extracted with more ether and finally with ethyl acetate. The organic layers were combined, dried over sodium sulfate, and concentrated to afford 33.8 g of an oil. Chromatography on a column of silica gel eluting with ethyl acetate-hexane followed by ethyl acetate, afforded 8.0 g of the title compound as a colorless oil. An analytical sample was obtained by semi-preparative HPLC, $[\alpha]_D$ −17.3° (c=1.06, chloroform).

Example 1g (1S-trans)-3,3-Diethoxy-1,2-cyclobutanedimethanol,-dibenzoate ester (1S-trans)-3,3-Diethoxy-1,2-cyclobutanedimethanol (35.1 g) was dissolved in 250 ml of dry pyridine, cooled to 0° C. under argon, and treated over 0.5 hours with benzoyl chloride (59.7 ml). The cooling bath was removed and the mixture was stirred at ambient temperature for 2.5 hours. The mixture was then cooled to 0° C. and treated over 5 minutes with 125 ml of water. The cooling bath was removed and the mixture was stirred at ambient temperature for 18 hours. The mixture was concentrated in vacuo ad the residue was co-distilled with water (×3) and with toluene (×2) in vacuo. The residue was partitioned between ethyl acetate and water. The organic layer was washed with 10% sodium bisulfate (2×250 ml), water (4×250 ml), saturated sodium bicarbonate (2×250 ml), and water (3×250 ml). Drying over sodium sulfate, concentration in vacuo, and azetroping with carbon tetrachloride gave 83 g of the title compound as a semi-solid.

Example 1h (2S-trans)-2,3-Bis(benzoyloxymethyl)cyclobutanone

The above sample of (1S-trans)-3,3-diethoxy1,2-cyclobutanedimethanol, dibenzoate ester (83 g) was dissolved in acetonitrile (1.75 L) under argon and treated with 660 ml of 0.5 N sulfuric acid. The mixture was stirred at ambient temperature for 17 hours and then was diluted with 5L of ethyl acetate. This solution was washed with water (2×1 L), saturated sodium bicarbonate (1 L), water (2×1 L), and brine (1 L). The organic phase was dried over sodium sulfate and evaporated to a white solid in vacuo. Partial dissolution in 400 ml of ether and cooling at −30° C. for 2 hours gave a solid which was filtered, washed with cold ether, and dried in air to give 46.4 g of the title compound, m.p. 93°-94° C., $[\alpha]_D$=+22.8° (c=1.0, $CHCl_3$).

Another 8 g of slightly impure title compound was obtained by evaporation of the filtrate to a solid residue.

Example 1i

[1S-(1α,2β,3β)]-3-hydroxy-1,2-cyclobutanedimethanol, 1,2-dibenzoate ester (2S-trans)-2,3-Bis(benzoyloxymethyl)cyclobutanone (33.81 g) in 440 ml of dry tetrahydrofuran at −78° C. under argon was treated with 100 ml of 1M lithium trisiamylborohydride in tetrahydrofuran over 20 minutes. After stirring another 10 minutes at −78° C., the mixture was warmed to room temperature, and 100 ml of saturated sodium bicarbonate was added over 5 minutes. The resultant mixture was cooled in an ice-acetone bath and treated with 36.5 ml of 30% hydrogen peroxide at a rate so as to maintain the temperature at 25°-30° C. After the addition, the mixture was diluted with 300 ml of water and extracted with 1.1 L of ethyl acetate. The organic phase was washed with water (×3), dried over sodium sulfate, and concentrated to a colorless oil (35 g). The oil was taken up in 100 ml of hexane/ethyl acetate (2/1) and filtered through a 1 L pad of silica gel(K-60), eluting with the same solvent mixture. Evaporation of the appropriate fractions gave 27 g of pure title compound as a colorless oil. Another 4.4 g of slightly impure material gave 3.4 g of the pure title compound after column chromatography using the same solvent system.

Example 1j

[1S-(1α,2β,3β)]-3[[(4-Methylphenyl)sulfonyl]-oxy]-1,2-cyclobutanedimethanol, dibenzoate ester

[1S-(1α,2β,3β)]-3-hydroxy-1,2-cyclobutanedimethanol, 1,2-dibenzoate ester (27 g) was dissolved in 110 ml of dry pyridine under argon and treated with p-toluenesulfonyl chloride (16.7 g). The mixture was heated and stirred at 60° for 16 hours, cooled to 40° C., and treated with 2 ml of water. After stirring for 2 hours at 40° C. the mixture was concentrated in vacuo to an oil. After azetroping with 2×150 ml of water in vacuo, the residue was partitioned between water and ethyl acetate. The organic phase was washed with water (×2), saturated sodium bicarbonate (×2), and brine. Drying over sodium sulfate and evaporation n vacuo gave 32.2 g of an oil. Trituration with pentane gave 28.3 g of a solid. Crystallization from ethyl acetate/pentane gave 18.4 g of pure title compound as a solid, m.p. 91°-92° C., $[\alpha]_D$=+13.8° (c=1.3, $CHCl_3$). Another 4 g of title compound was obtained by chromatography of the mother liquors on silica gel using hexane/ethyl acetate (3/1).

Example 1k 1R-(1α,2β,3α)]-1-[2,3-Bis[(benzoyloxy)methyl]-cyclobutyl]-2,4(1H,3H)-pyrimidinedione To 2.26 g (20 mmol) of uracil in 83 ml of dimethylformamide was added a solution of 40% n-tetrabutylammonium hydroxide in water (11.8 ml, 18 mmol). The mixture was stirred at room temperature for 30 minutes, and the clear solution was concentrated at 50° C./1 mm. Dimethylformamide (40 ml) was added to the residue, and concentration under vacuum was repeated. This process was repeated 4 more times, and the residue was then dried overnight at room temperature in vacuo to give uracil, tetra-n-butylammonium salt.

To uracil, tetra-n-butylammonium salt under argon was added 25 ml of dry dimethylformamide, followed by 2.50 g of ca. 90% pure [1S-(1α,2β,3α)]-3-[[(4-methylphenyl)sulfonyl]-oxy]-1,2-cyclobutanedimethanol, dibenzoate ester (ca. 4.55 mmol). The mixture was stirred at 75° C. for 24 hours, cooled to room temperature, and left to stand overnight. Acetic acid (2.0 ml, 35 mmol) was added, the mixture was stirred for 5 minutes and the solvents were removed in vacuo at 50° C./1 mm. The resulting residue was taken up in ethyl acetate (70 ml) and water (70 ml). Slightly damp Bio-Rad AG-MP-50 (K+form) resin (ca. 51 g) was added, and stirring was continued for 1 hour. The mixture was filtered, and the layers in the filtrate were separated. The aqueous layer was extracted with ethyl acetate, and the ethyl acetate layers were combined, dried (sodium sulfate) and evaporated. Ethyl acetate was added to the residue, the resulting suspension was filtered and the filtrate was concentrated to give 3.35 g of oily product containing ca 0.4–0.5 equivalent of tetra-n-butylammonium salts. This material was dissolved in ethyl acetate (70 ml) and water (70 ml), and the pH was adjusted from 3.2 to 7.0 using 1N potassium hydroxide. Treatment with ca. 51 g of slightly damp Bio-Rad AG-MP-50 K+ form) resin, filtration and extraction of the aqueous layer with acetate provided 2.097 g of crude product upon evaporation. This material was applied in ethyl acetate (45 ml) to a column of Merck silica gel (285 g, packed in toluene). Elution with toluene, and then 2 and 4% isopropyl alcohol in toluene, afforded 701 mg of the title compound.

Example 1l 1R-(1α,2β,3α)]-1-[2,3-Bis(hydroxy)methyl]-cyclobutyl]-2,4(1H,3H]-pyrimidinedione To a suspension of 1R-(1α,2β,3α)]-1-[2,3-bis[(benzoyloxy)methyl]cyclobutyl]-2,4(1H,3H)-pyrimidinedione (701 mg, 1.62 mmol, dried by concentration in vacuo from 20 ml of dry toluene) in dry methanol (20 ml) was added 209 μl of a solution of 25% sodium methoxide in methanol. The mixture was stirred at 40° C. for 5 hours, and then additional 25% sodium methoxide in methanol (105 μl) was added. Heating was continued for 1 hour, the mixture was cooled to room temperature and finally concentrated in vacuo to a residue. Water (5 ml) was added, the pH was adjusted to 7.0 with 1N hydrochloric acid, and the mixture was stored overnight at −20° C. The pH (5.8) was adjusted to 7.2 using 0.5N sodium hydroxide, and the mixture was applied in water to a column of CHP-20P resin (160 ml), Mitsubishi Chemical Co.; 35–150μ packed in water. Elution with water and then 2 and 4% acetonitrile in water afforded, after removal of acetonitrile in vacuo and lyophilization, a residue, which was dissolved in acetonitrile and water. Concentration of this solution gave 342 mg of the title compound as a solid.

Example 1m

[1R-(1α,2β,3α)]-1-[2,3-Bis(hydroxymethyl)-cyclobutyl-5-iodo-2,4(1H,3H)-pyrimidinedione To a suspension of 1R-(1α,2β,3α)]-1-[2,3-bis(hydroxy)methyl]cyclobutyl]-2,4(1H,3H)-pyrimidinedione (338 mg, 1.50 mmol) in dioxane (30 ml, purified by passage through basic alumina) was added iodine (762 mg, 3.0 mmol) and 0.8M nitric acid (2.0 ml, 1.6 mmol). The mixture was stirred under argon at 95° C. for 2 hours and then cooled to room temperature. The pH was adjusted to 6.5 using saturated aqueous sodium bicarbonate, and the mixture was concentrated in vacuo to a residue. The mixture was concentrated repeatedly in vacuo from mixtures of ethanol-chloroform yielding a dark brown residue, which was applied as a suspension in water to a column of CHP-20P resin (150 ml, Mitsubishi Chemical Co., 35–150μ) packed in water. Elution with water and then 10 and 20% acetonitrile in water gave 456 mg of desired product containing a small amount of iodine. Passage of this material through a 150 ml column of CHP-20P resin using water and then 10 and 20% acetonitrile in water afforded, after concentration in vacuo, 419 mg of the title compound free of iodine.

Example 1n

[1R-(1α(E),2β,3α)]-3-[1-[2,3-Bis(hydroxymethyl)cyclobutyl-1,2,3,4-tetrahydro-2,4-dioxo-5-pyrimidinyl]-2-propenoic acid, methyl ester Dry dioxane (3.5 ml, purified by passage through basic alumina) was deoxygenated in vacuo. To the deoxygenated dioxane under argon was added 13 mg (0.058 mmol) of palladium (II) acetate, 30 mg (0.116 mmol) of triphenylphosphine, and 0.21 ml (1.47 mmol) of triethylamine (freshly distilled from calcium hydride). The mixture was placed in a bath at 70° C. and stirred for 15 minutes to give a deep red solution. [1R-(1α,2β,3α)]-1-[2,3-Bis(hydroxymethyl)cyclobutyl]-5-iodo-2,4(1H,3H)-pyrimidinedione (379 mg, 1.08 mmol, previously dried over phosphorus pentoxide at 55° C./1 mm for 2 hours) was added, followed by methyl acrylate (194 μl, 2.16 mmol), and the mixture was stirred at 70° C. for 4 hours. The reaction was cooled to room temperature and stored overnight at −20° C. After warming to room temperature, the reaction was diluted with dichloromethane and filtered through Celite. Water and acetonitrile were added to the filtrate to dissolve small amounts of oily residue, and the filtrate was concentrated in vacuo (697 mg). The Celite was washed with acetonitrile, and the washes were evaporated (14 mg). The 697 mg and 14 mg residues were combined using acetonitrile-water and concentrated in vacuo. Treatment of this residue with methanol gave, after collection by filtration, 195 mg of desired product as a solid. Evaporation of the filtrate gave a residue (435 mg), which was treated with methanol to give 29 mg of additional desired product and 394 mg of residue after concentration of the filtrate. Chromatography of the 394 mg fraction on a column of Merck silica gel (40 g, packed in dichloromethane) using dichloromethane and then 5, 6 and 7% methanol in dichloromethane afforded 64 mg of material consisting of ca. 45 mg of desired product and ca. 19 mg of triethylammonium iodide.

Example 1o

[1R-(1α(E),2β,3α)]-3-[1-[2,3-Bis(hydroxymethyl)cyclobutyl]-1,2,3,4-tetrahydro-2,4-dioxo-5-pyrimidinyl]-2-propenoic acid A solution of [1R-(1α(E),2β,3α)]-3-[1-[2,3-bis(hydroxymethyl)cyclobutyl]-1,2,3,4-tetrahydro-2,4-dioxo-5-pyrimidinyl]-2-propenoic acid, methyl ester (230 mg, 0.74 mmol) in 2.6 ml of 2N potassium hydroxide was stirred at room temperature for 1 hour and then cooled to 0°-5° C. The pH was adjusted to 2.0 using 6N hydrochloric acid, and the mixture was stirred at 0°-5° C. for 30 minutes. The solids were collected by filtration, washed with ca. 2 ml of cold water, air dried, and then dried over phosphorus pentoxide overnight at 35° C./ 1 mm to give 205 mg of the title compound.

Example 1p

[1R-(1α(E),2β,3α)]-1-[2,3-Bis(hydroxymethyl)cyclobutyl]-5-(2-bromoethenyl)-2,4(1H,3H)pyrimidinedione To a stirred solution of [1R-(1α(E),2β,3α)]-3-[1-[2,3-bis(hydroxymethyl)cyclobutyl]-1,2,3,4-tetrahydro-2,4-dioxo-5-pyrimidinyl]-2-propenoic acid (196 mg, 0.66 mmol) in 3.6 ml of dry dimethylformamide under argon at room temperature was added 198 mg (1.98 mmol) of potassium bicarbonate. The mixture was stirred for 5 minutes and then N-bromosuccinimide (118 mg, 0.66 mmol) was added. The mixture was stirred for 6 hours at room temperature and stored overnight stored overnight at −80° C. The solvent was removed in vacuo (50° C./1 mm), water was added and the mixture was concentrated in vacuo. The resulting residue was taken up in 15% acetonitrile in water and applied to a column of CHP-20P resin (35 ml) packed in water. Elution with a gradient of water to 50% acetonitrile in water followed by lyophilization, gave 161 mg of the title compound as a solid having m.p. 141°-142° C. and $[\alpha]D^{22}=-45°$ (C=0.31, methanol). Calculated for $C_{12}H_{15}BrN_2O_4.0.68\ H_2O$: C, 41.96; H. 4.80; N, 8.16 Found: C,41.96; H, 4.70; N, 8.16.

$^1H$ NMR (270 MHz, DMSO-$d_6$) δ 11.46 (1H, s, NH), 8.03 (1H, s, H-6), 7.27 (1H, d, J=13.49, vinylic H), 6.93 (1H, d, J=13.49, vinylic H), 4.60 (2H, m, 2 OHs), 4.49 (1H, m, H-1'), 3.46 (4H, m, 2 $CH_2O$), 2.49 (1H, m H-2'or H-3'or H-4'under solvent), 2.23 (1H, m, H-2' or H-3' or H-4'), 1.94 (1H, m, H-2' or H-3' or H-4'), 1.80 (1H, m, H-2' or H-3' or H-4').

EXAMPLE 2

Treatment of Viral Infection in Cell Culture in Vitro

Assays were performed in cell culture systems to determine the concentrations of compounds that are effective in presenting several kinds of viral infections. The assays are described below, and the results are presented in Table 1.

TABLE 1

Abbreviations:

HSV-1 (herpes simplex virus type 1, strain Schooler), VZV (varicella zoster virus, strain ELLEN).

Cell Culture Assays:

HSV-1 and VZV antiviral assays: Virus was adsorbed to WI-38 cell culture monolayers in 6 well culture plates (Costar, Cambridge, MA) for 1 hour prior to addition of maintenance medium containing duplicate dilutions of the test compound. Inhibition of plaque development was evaluated on fixed and stained monolayers after 4 days incubation at 37° C. for HSV-1 and after 6-7 days incubation at 37° C. for VZV. $ID_{50}$ values were determined from the drug concentration which conferred at least a 50% plaque reduction compared to virus controls.

Antiviral Activity of Compound 1, [1R-(1α(E), 2β, 3α)]-1-[2,3-Bis(hydroxymethyl)cyclobutyl]-5-(2-bromoethenyl)-2,4(1H, 3H)-pyrimidinedione, Against HSV-1 and VZV

| Virus | $ID_{50}$ (μM) |
|---|---|
| HSV-1 | 0.3 |
| VZV | 0.06-0.15 |

What is claimed is:

1. [1R-(1α(E),2β,3α)]-1-[2,3-bis(hydroxymethyl)cyclobutyl]-5-(2-bromoethenyl)-2,4(1H,3H)pyrimidinedione.

* * * * *